United States Patent [19]

Edwards

[11] Patent Number: 4,803,066
[45] Date of Patent: Feb. 7, 1989

[54] ANTIBACTERIAL AND/OR ANTIFUNGAL COMPOSITIONS FOR TOPICAL APPLICATION

[75] Inventor: Linda M. Edwards, Saffron Walden, United Kingdom

[73] Assignee: Smith & Nephew Associated Companies p.l.c., England

[21] Appl. No.: 27,861

[22] Filed: Mar. 19, 1987

[30] Foreign Application Priority Data

Mar. 22, 1986 [GB] United Kingdom ............... 8607159

[51] Int. Cl.$^4$ ............................................. A61K 33/04
[52] U.S. Cl. .................................... 424/132; 424/164; 424/464; 424/DIG. 13; 514/183; 514/359; 514/396; 514/886; 514/887; 514/937; 514/938; 514/944; 514/959; 514/969
[58] Field of Search ....... 424/132, 164, 464, DIG. 13; 514/183, 359, 396, 886, 887, 937, 938, 944, 959, 969

[56] References Cited

U.S. PATENT DOCUMENTS 4,419,352 12/1983 Cox et al. ............................. 514/228
4,438,258 3/1984 Graham ............................... 524/593

FOREIGN PATENT DOCUMENTS 170139 2/1986 European Pat. Off. .
2319852 10/1973 Fed. Rep. of Germany .
2558058 1/1984 France .

OTHER PUBLICATIONS

Experimentia 1978 34(4) 472-73 S, Yamashita et al "Antimicrobial Activity of Metal Derivatives of Sulphonamides".

Primary Examiner—John Kight
Assistant Examiner—S. A. Acquah
Attorney, Agent, or Firm—Jacobs & Jacobs

[57] ABSTRACT

Pharmaceutical compositions which are suitable for topical application in the treatment of bacterial and/or fungal infections are described. The compositions comprise a synergistic mixture of a silver compound and an azole derivative together with a pharmaceutically acceptable carrier therefor. The compositions may be applied topically in the treatment of burns ulcers and other skin lesions, general skin infections and also in the treatment of infections of the mucous membranes. Preferred compositions contain silver sulphadiazine and clotrimazole or metronidazole. The compositions may be applied as ointments, gels, pessaries, tablets and the like.

26 Claims, No Drawings

ANTIBACTERIAL AND/OR ANTIFUNGAL COMPOSITIONS FOR TOPICAL APPLICATION

This invention relates to pharmaceutical compositions which are suitable for topical application in the treatment of bacterial and/or fungal infections and which contain a synergistic mixture of a silver compound, particularly a silver sulphonamide and an azole derivative particularly clotrimazole.

The antimicrobial effect of silver ions is well known. An excellent product containing silver sulphadiazine is available from Smith & Nephew Pharmaceuticals Ltd., Harold Hill, U.K., under the registered trade mark 'Flamazine'. However, some authorities believe that resistant organisms may arise and that it would be advantageous to include a second antimicrobial agent along with the silver salt. Surprisingly we have found that by including an azole derivative with a silver salt in a pharmaceutical composition a synergistic antibacterial and antifungal effect is achieved against several important pathogenic organisms. The use of an azole derivative gives an added advantage that the composition may be used against topical fungal infections as well as against topical bacterial infections.

Accordingly the present invention provides a pharmaceutical composition suitable for topical application which comprises a synergistic mixture of an antimicrobial silver compound and an antimicrobial azole compound or a pharmaceutically acceptable acid addition salt thereof and a topically acceptable carrier therefor.

In one aspect of the invention the compositions contain an azole compound of formula (I) as hereinafter defined. The preparation of compounds of formula (I) are described in for example British Pat. Nos. 1170188 and 1244530.

Accordingly in one aspect the present invention provides a pharmaceutical composition suitable for topical application which comprises a synergistic mixture of a silver compound and an azole compound of formula (I)

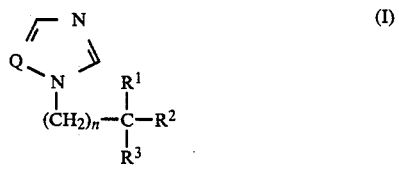

or a pharmaceutically acceptable acid addition salt thereof, wherein Q is CH or N, n is 0 or 1, $R^1$ is lower alkanoyl, lower alkyl hydroxy, phenyl or phenyl lower alkyl wherein the phenyl groups are optionally substituted with up to 3 halogen atoms, $R^2$ is aryl, aryloxy, aryl thio, aryl lower alkyloxy or aryl lower alkylthio, wherein aryl is phenyl, thienyl, or halo thienyl and $R^3$ is hydrogen, lower alkynyl, lower alkoxy carbonyl or phenyl, the phenyl group being optionally substituted with up to 3 substituents each independently selected from halogen or trifluoromethyl; and a topically acceptable carrier therefor.

In the definitions given above the term halogen is generic to fluoro, chloro, bromo and iodo and the term 'lower alkyl' means straight and branched chain hydrocarbon radicals having from 1 to 4 carbon atoms.

Most aptly Q is CH. Most aptly $R^1$ is mono or dihalophenyl and is preferably mono or dichlorophenyl. Most aptly $R^3$ is hydrogen or phenyl or mono or dihalophenyl and is preferably phenyl, chlorophenyl or dichlorophenyl. Most aptly $R^2$ is phenylmethoxyl, monohalo phenylmethoxy or dihalophenylmethoxy and is preferably mono or dichlorophenylmethoxy.

Preferred compositions are those in which the azole derivative is a compound of formula I wherein Q is CH, n is 1, $R^1$ is mono- or dihalophenyl, $R^2$ is (mono- or dihalophenyl) methoxy and $R^3$ is hydrogen. Particularly preferred compositions are those in which Q is CH, n is 1, $R^1$ is 2,4-dichlorophenyl, $R^2$ is (mono- or dichlorophenyl) methoxy and $R^3$ is hydrogen.

Other favoured compositions are those in which the azole derivative is a compound of formula I wherein Q is CH, n is 0, $R^1$ is mono or dihalophenyl, $R^2$ and $R^3$ are phenyl.

Preferably the azole is an imidazole that is Q is CH.

The compounds of formula (I) may be present as a pharmacuetically acceptable acid addition salt as a salt of an organic acid such as acetic, propanoic, gluconic and lactic acids or an inorganic acid such as sulphuric and nitric acids.

A preferred azole is 1-{(2-chlorophenyl)diphenylmethyl}-1H-imidazole, commonly known as clotrimazole. A second preferred azole is 1-{2-(2,4-dichlorophenyl)-2-[(2,4-dichlorophenyl)methoxy]ethyl}-1H-imidazole, commonly known as miconazole and especially its nitrate salt. A third preferred azole is 1-{2-(2,4-dichlorophenyl)-2-[(4-chlorophenyl)methoxy]ethyl}-1H-imidazole, commonly known as econazole and especially its nitrate salt.

In another aspect of the present invention the compositions contain an azole compound of formula (II) as hereinafter defined. The preparation of compounds of formula (II) is described in for example, U.S. Pat. No. 2944061.

Accordingly in another aspect the present invention provides a pharmaceutical position suitable for topical application which comprises a synergistic mixture of a silver compound and an azole compound of formula (II).

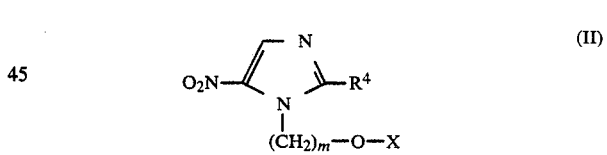

or a pharmaceutically acceptable and addition salt thereof in wich $R^4$ is hydrogen or lower alkyl, m is 2 to 4 and X is hydrogen or an acyl residue of a monocarboxylic or dicarboxylic aliphatic acid or aromatic acid; and a topically acceptable carrier therfor.

Aptly $R^4$ is methyl or ethyl. Aptly X is hydrogen or a lower aliphatic monocarboxyl residue such as acetyl or dichloracetyl, higher aliphatic monocarboxyl residue such as pivaloyl, aliphatic dicarboxyl residue such as succinyl, aromatic monocarboxyl residues such as benzoyl and its substitution derivatives such as salicyl, chlorobenzoyl, methoxybenzoyl, nitrobenzoyl and aromatic dicarboxyl residues such as phthalyl.

A preferred azole is one in which $R^4$ is methyl, m is 2 and X is hydrogen, namely 1-(2-hyderoxyethyl)-2-methyl-5-nitroimidazole(metronidazole) or a pharmaceutically acceptable acid addition salt therfor.

Suitable pharmaceutically acceptable and addition salts includes those described above.

By topical administration it is meant to include as well as application to lesions of the skin such as wounds, burns, surgical trauma and general skin infections, but also administration to the vagina, rectum and other mucous membranes.

The silver compound present in the compositions of the invention may be any of those which is suitable for topical application in, for example, the treatment of burns, including silver salts such as silver nitrate, silver sulphate, silver phosphanilide and the like, silver sulphonamides such as silver sulphadiazine. More suitable silver compounds are silver sulphonamides and preferred is silver sulphadiazine.

Suitably, the amount of silver compound which will be present in the compositions of the present invention will be from 0.1 to 10% by weight of the silver compound, more suitably will be from 0.2 to 5% by weight and preferably will be from 0.5 to 3.0% by weight for example 0.5%, 1%, 1.5%, 2.0% and 2.5%.

Suitably the amount of azole compound which will be present in the compositions of the present invention will be from 0.1 to 10% by weight of the azole compound, more suitably will be from 0.2 to 5% by weight and preferably will be from 0.5 to 3.0% by weight, for example 0.5%, 1%, 1.5%, 2.0% and 2.5%.

Suitably the ratio by weight of silver compound to azole compound in the composition of the present invention will be in the range from 10:1 to 1:10, more suitably will be in the range 5:1 to 1:5 and will preferably be from 2:1 to 1:2 for example 1:1.

The pharmaceutical compositions of the present invention are suitable for topical treatment of burns, ulcers and other skin lesions exposed to the risk of infection. The presence of a fungicidal azole compound means that the compositions may be used topically on the skin and it is also envisaged that they may be applied intravaginally and rectally.

Suitable forms of the topical composition of this invention include ointments, gels, oily suspensions, solid forms, for example tablets, powder, granules, pessaries, suppositories and the like, emulsions, lotions and films. The synergistic mixture may also be incorporated into medicated dressings and into adhesives used on polymeric film dressings such as 'OpSite'.

A topically administratable composition of the invention will preferably be in the form of an ointment. This will conveniently have a hydrophilic ointment base such as an oil-in-water emulsion. Suitable ointment bases are described in Chapter 87 Ointments: Emulsion Bases in Remingtons Pharmaceutical Sciences, 15th Ed. 1975, pages 1532-34. Also suitable ointment bases include those described in British Pat. No. 1240545 as suitable for use with silver sulphadiazine and which is incorporated herein by cross reference.

A particularly suitable ointment base is therefore an oil-in-water emulsion containing from 0 to 25% of petrolatum or liquid paraffin, 2 to 20% of a fatty alcohol, 0 to 12% of an emulsifying agent, up to 10% of non-ionic surfactant and 5 to 25% of a polyhydric alcohol and the balance to 100% being deionised or distilled water. Aptly the fatty alcohols are those conventionally used in ointments and are water insoluble. Suitable alcohols include stearyl alcohol, cetyl alcohol, lauryl alcohol and myristyl alcohol. Suitably the emulsifying agent is a glyceryl fatty acid ester and is preferably glyceryl monostearate. Suitable non-ionic surfactants include the polyoxyethylated sorbitan fatty acid esters and sorbitan fatty acid esters. An emulsifying wax may be used in place of both or part of both of the fatty alcohol and non-ionic surfactant. The polyhydric alcohol acts as a humectant and suitable alcohols include propylene glycol, sorbitol or glycerin or mixtures thereof.

In a second aspect the compositions of the present invention will be in the form of an aqueous gel. Suitable gelling agents include polyoxyethylene-polyoxypropylene diol block copolymers, polyacrylic acid lightly cross-linked with triallyl sucrose which has been neutralised using an alkali metal hydroxide, cellulosic derivatives such as carboxymethyl cellulose, hydroxymethyl cellulose, natural gums and the like. It will be appreciated that care must be taken to avoid using gelling agents which are incompatible with silver ions. A preferred group of gelling agents are the polyoxyethylene-polyoxypropylene diol block copolymers which are commercially available as the Pluronics from BASF-Wyandotte. (Pluronic is a registered trade mark of BASF-Wyandotte).

Suitable gel forming block copolymers of polyoxyethylene-polyoxypropylene will have a molecular weight from 4,600 to 13,500 (approximately) and will be present in the gel in an amount from 50% for the lower molecular weight copolymers to 20% for the higher molecular weight copolymers, so that the gel when applied topically is neither too stiff nor too fluid. Typically the gels are formed by mixing together the copolymer and water to form an aqueous solution at a temperature of 2° C. and adding the silver compound and azole compound and then allowing the solution to gel as it warms to ambient temperature. Suitable Pluronics are those designated as F108, F127 and P105.

In a further aspect the composition of the present invention will be in the form of a hydrophobic ointment. Suitable hydrophobic ointments are those which are formed from white or yellow soft paraffin or a mixture of such with liquid paraffin. A preferred ointment base comprises a mixture of white soft paraffin and liquid paraffin in a ratio of 5:1 to 1:1. However, in general terms aqueous based systems will be preferred.

The hydrophobic ointment base may also contain non-ionic surfactants such as polyoxyethylated sorbitan fatty acid esters and sorbitan fatty acid esters. The presence of non-ionic surfactants increases the miscibility of the ointment with wound fluid and aids release of the medicament. Suitably the non-ionic surfactant will be present in an amount from 0.1 to 0.5%. Preferably the non-ionic surfactant is 0.1% of polyoxyethylene sorbitan trioleate and 0.1% sorbitan monopalmitate.

A more hydrophilic ointment may contain from 1 to 5% of a non-ionic surfactant. Suitable ointments are described in for example British Pat. No. 1599159.

The synergistic mixture may also be present in a pessary. Thus in a further aspect of the invention the composition is in the form of a pessary which contains a synergistic mixture of a silver compound and an azole compound or a pharmaceutically acceptable acid addition salt. Pessaries are formed in a conventional manner including mixing a molten wax which melts at body temperature with the active ingredients and forming in a mould.

In a further aspect therefore the present invention comprises a method of treatment which comprises applying topically a pharmaceutical composition which comprises a synergistic mixture of a silver compound and an azole compound.

The method is applicable to treatment of lesions of the skin as hereinbefore defined, general skin infections and infections associated with the mucous membranes such as the vagina and rectum.

It will be appreciated that in the types of compositions hereinbefore described there will not be presence in the composition anything which is incompatible with the silver ion, that is that will lead to the formation of an insoluble salt or a light unstable compound.

The active ingredients may be incorporated into the composition by such conventional methods as mixing with the carrier, for example the silver compound and azole compound may be added to an ointment base and stirred until a homogeneous mixture is formed.

The silver compound and azole compound content of the compositions of this invention will be an antimicrobially effective amount, that is to say from 0.1 to 10%, suitably the compositions will contain 0.2 to 5%, more suitably 0.5 to 3.0% and preferably 1 or 2%. The percentage terms herein are expressed as a weight/weight basis.

From the foregoing it is clear that in a favoured aspect the present invention comprises a pharmaceutical composition adapted for topical administration for the treatment of burns, ulcers and other skin lesions exposed to the risk of infection which comprises from 0.5 to 3% of a silver compound, 0.5 to 3% of an azole compound or pharmaceutically acceptable salt thereof, 15 to 25% of liquid paraffin, 7 to 15% polyhydric alcohol, 4 to 8% of stearyl alcohol, 4 to 8% of glyceryl monostearate, 2 to 6% of a non-ionic surfactant and water to adjust the weight to 100%.

The present invention also provides a method of treating burns, ulcers or other skin lesions which comprises applying thereto a composition of this invention. This treatment will aid in keeping the lesion uninfected.

In a further aspect therefore, the present invention provides a method of treating burns, ulcers, or other skin lesions which comprises applying topically thereto a pharmaceutical composition comprising a synergistic antimicrobially effective amount of silver compound and an azole compound as hereinbefore described together with a topically acceptable carrier therefor.

In another aspect the composition of the present invention may additionally contain other medicaments which are active when applied topically, for example antimicrobial agents, anti-inflammatories and the like.

EXAMPLE 1

Oil-in-water Emulsion Ointment Composition

The percentage composition of the ointment is as follows:

|  | % (w/w) |
| --- | --- |
| Silver sulphadiazine | 1.0 |
| Clotrimazole | 1.0 |
| Liquid paraffin | 6.0 |
| Cetostearyl alcohol | 7.2 |
| Cetomanogol | 1.8 |
| White-soft paraffin | 15.0 |
| Glycerol | 5.0 |
| Water to | 100.0 |

The water, for example, distilled water, which had been preheated to 80° C. is added to a vessel. The silver sulphadiazine and clotrimazole are mixed with the glycerol to form a smooth homogeneous suspension and this is then added to the stirred water in the mixing vessel.

The alcohols and paraffin are melted together and heated to 70° C. The molten mixture is added to the aqueous component with stirring. Initially stirring is vigorous but as the mixture cools and thickens the rate of stirring is reduced.

The ointment may then be poured into presterilised containers such as cylindrical pots or plastic tubes.

EXAMPLE 2

Aqueous Gel Composition

An aqueous gel was prepared which had the following composition,

| Hydroxyethyl cellulose | 2.0% |
| --- | --- |
| Propylene glycol | 10.0% |
| Clotrimazole | 1.0% |
| Silver sulphadiazine | 1.0% |
| Distilled water to | 100.0% |

The hydroxyethyl cellulose (2 g) was dissolved with stirring in a major portion of the distilled water (80 g). The clotrimazole (1 g) and silver sulphadiazine (1 g) were dispersed propylene glycol (10 g) to form a homogeneous suspension. This suspension was added to the hydroxyethyl cellulose solution with stirring to provide a homogeneous gel mixture and finally the weight of the gel was adjusted to 100 g by addition of further distilled water.

The gel may be packaged in a similar manner to that described in Example 1.

EXAMPLE 3

Hydrophobic Ointment Composition

| Silver sulphadiazine | 1.0% |
| --- | --- |
| Clotrimazole | 1.0% |
| Liquid paraffin/ white soft paraffin | (1:4 mixture) to 100% |

The paraffin components are melted together and thoroughly mixed. The silver sulphadiazine and clotrimazole are added and the mixture stirred until it is homogeneous. The ointment composition is then allowed to cool and the ointment may be packaged in a similar manner to that described in Example 1.

EXAMPLE 4

Pessary Composition

A pessary is prepared which has the following composition:

| Silver Sulphadiazine | 100 mg |
| --- | --- |
| Clotrimazole | 100 mg |
| Massa estarinium B to | 4 g |

EXAMPLE 5

Oil-in-water Emulsion Ointment Composition

An ointment was prepared in a similar manner to that described in Example 1 except that the ointment contained silver sulphadiazine 1.5% and miconazole nitrate 1.5% as the active ingredients.

EXAMPLE 6

Oil-in-water Emulsion Ointment Composition

An ointment was prepared in a similar manner to that described in Example 1 except that the ointment contained silver sulhadiazine 2.0% and econazole nitrate 2.0% as the active ingredients.

EXAMPLE 7

Oil-in-water Emulsion Ointment Composition

An ointment was prepared in a similar manner to that described in Example 1 except that the ointment contained 2.0% silver nitrate and 2.0% miconazole nitrate as the active ingredients.

EXAMPLE 8

Oil-in-water Emulsion Ointment Composition

An ointment was prepared in a similar manner to that described in Example 1 except that the ointment contained 2.0% silver nitrate and 2.0% clotrimazole.

EXAMPLE 9

Aqueous Gel Composition

An aqueous gel was prepared in a similar manner to that described in Example 2 except that the gel contained silver nitrate 1.5% and miconazole nitrate 1.5%.

EXAMPLE 10

Hydrophobic Ointment Composition

A hydrophobic ointment was prepared in a similar manner to Example 3 except that the ointment contained silver sulphadiazine, 1.0÷ and aconazole nitrate, 1.0% as active ingredients.

EXAMPLE 11

Hydrophilic Ointment Composition

A hydrophilic ointment is prepared by melting together and thoroughly mixing until homogeneous the following ingredients:

| Silver sulphadiazine | 1.5% |
| Clotrimazole | 1.0% |
| Sorbitan monopolmitate | 2.0% |
| White soft paraffin | 95.5% |

The ointment composition is then allowed to cool and the ointment may be packaged in a similar manner to that described in Example 1.

EXAMPLE 12

Pessary Composition

A pessary is prepared which has the following composition:

| Silver sulphadiazine | 100 mg. | |
| Miconazole nitrate | 150 mg. | g. |
| Massa estarinium B | to 4 g. | to 4 g. |

EXAMPLE 13

Oil-in-water Emulsion Ointment Composition

The percentage composition of an ointment is as follows:

| | % (w/w) |
| --- | --- |
| Silver sulphadiazine | 1.0 |
| Metronidazole | 1.0 |
| Liquid paraffin | 7.0 |
| Cetostearyl alcohol | 7.2 |
| Cetomonogol | 1.5 |
| White-soft paraffin | 14.3 |
| Glycerol | 5.0 |
| Water to | 100.0 |

The ointment was prepared in a similar manner to that described in Example 1. The sterile ointment may be packed in presterilised containers such as cylindrical pots or plastic tubes.

EXAMPLE 14

Pessary Composition

A pessary is prepared which has the following composition:

| Silver sulphadiazine | 200 mg |
| Metronidazole | 200 mg |
| Massa estarinium B to | 4 g |

Demonstration of Effectiveness

The minimum inhibitory concentration (MIC) of silver sulphadiazine and clotrimazole individually and in combination were obtained against six test organisms, three different strains of *Candida albicans*, two strains of *Staphylococcus aureus* and a strain of Enterococcus. The test method employed was as follows suspensions of each agent or combination of agents were prepared at a range of dilutions in 60% propylene glycol in water. Isosensitest (trade mark) broth was inoculated with a test organism at a concentration of $10^5$ organisms per ml and a sample was dispensed into wells of a microliter plate. The range of concentration of test substance or combination was added to the wells so that there was a further 10-fold dilution of the test substance or combination. The plates were incubated for either 24 or 48 hours at 37° C., and the MIC read as the lowest concentration giving no visible growth. For each organism tested all conditions of inoculum preparation, inoculation and incubation were standardised throughout.

The results of the tests are given in Table 1.

TABLE 1

Minimum inhibitory concentrations (MIC) of silver sulphadiazine and clotrimazole, both alone and in combination, against a range of organisms.

| | MIC: Individual Agents ($\mu g\ ml^{-1}$) | | MIC: Combination of Agents ($\mu g\ ml^{-1}$) | |
| --- | --- | --- | --- | --- |
| Organism | Silver Sulphadiazine | Clotrimazole | Silver Sulphadiazine | Clotrimazole |
| *C. albicans* I | 100 | 5 | 6.25 | 0.156 |
| V | 10 | 0.5 | 1.25 | 0.0625 |
| 159 | 250 | 25 | 15.63 | 1.56 |
| *Staph. aureus* | 100 | 100 | 12.5 | 12.5 |

TABLE 1-continued

| | MIC: Individual Agents ($\mu$g ml$^{-1}$) | | MIC: Combination of Agents ($\mu$g ml$^{-1}$) | |
|---|---|---|---|---|
| Organism | Silver Sulphadiazine | Clotrimazole | Silver Sulphadiazine | Clotrimazole |
| NCTC 10788 Staph. aureus 1300 | 100 | 100 | 25 | 25 |
| Enterococcus 0022 | 250 | 100 | 7.81 | 6.25 |

Minimum inhibitory concentrations (MIC) of silver sulphadiazine and clotrimazole, both alone and in combination, against a range of organisms.

The results show a synergistic effect between silver sulphadiazine and clotrimazole against these organisms.

The minimum inhibitory concentrations (MIC) of silver sulphadiazine and micronazole nitrate individually and in combination, silver sulphadiazine and econazole nitrate individually and in combination, and silver nitrate and clotrimazole individually and in combination were also determined against some of the test organisms, and in particular against Candida albicans, employing the method given above. The results of the tests are given in Tables 2–4.

TABLE 2

Minimum inhibitory concentrations (MICs) of silver sulphadiazine and miconazole nitrate, both alone and in combination.

| | MIC: Individual Agents ($\mu$g ml$^{-1}$) | | MIC: Combination of Agents ($\mu$g ml$^{-1}$) | |
|---|---|---|---|---|
| Organism | Silver Sulphadiazine | Miconazole nitrate | Silver Sulphadiazine | Miconazole nitrate |
| C. albicans V | 10 | 62.5 | 0.195 | 1.95 |
| Staph. aureus | 50 | >500 | 12.5 | 125 |
| E. Coli 0029 | 50 | >500 | 12.5 | 125 |

The results show a synergistic effect between silver sulphadiazine and miconazole against these organisms.

TABLE 3

Minimum inhibitory concentrations (MICs) of silver nitrate and clotrimazole, both alone and in combination.

| | MIC: Individual Agents ($\mu$g ml$^{-1}$) | | MIC: Combination of Agents ($\mu$g ml$^{-1}$) | |
|---|---|---|---|---|
| Organism | Silver nitrate | Clotriamazole | Silver nitrate | Clotrimazole |
| C. albicans V ATCC 10231 | 25 | 12.5 | 6.25 | 3.125 |

The results show a synergistic effect between silver nitrate and clotrimazole.

TABLE 4

Minimum inhibitory concentrations (MICs) of silver nitrate and clotrimazole, both alone and in combination.

| | MIC: Individual Agents ($\mu$g ml$^{-1}$) | | MIC: Combination of Agents ($\mu$g ml$^{-1}$) | |
|---|---|---|---|---|
| Organism | Silver nitrate | Clotrimazole | Silver nitrate | Clotrimazole |
| C. albicans V ATCC 10231 | 25 | 12.5 | 6.25 | 3.125 |

The results show a synergistic effect between silver nitrate and clotrimazole.

Test samples of silver sulphadiazine and metronidazole were placed in adjacent wells cut into agar plates seeded with one of the following organisms: Staphylococcus aureus NCTC 10788 and Pseudomonas aeruginosa 1644. The plates were incubated and examined for zones of inhibition. The plates showed that there was synergy between silver sulphadiazine and metronidazole against the above organisms.

This test method and the interpretation of results obtained is described in 'Antibiotics in Laboratory Medicine' edited by V. Lorion MD., in the section entitled 'Method for Assessing Antimicrobial Combinations'.

I claim:

1. A pharmaceutical composition in topical administration form which comprises a synergistic mixture of an antimicrobial silver compound and an antimicrobial azole compound or a pharmaceutically acceptable acid addition salt thereof in the weight ratio of 10:1 to 1:10; in combination with a topically acceptable carrier therefor.

2. A composition according to claim 1 wherein the azole is a compound of the the formula (I)

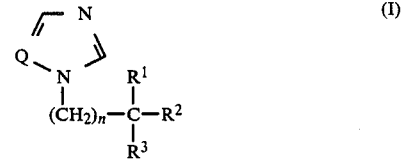

or a pharmaceutically acceptable acid addition salt thereof, wherein Q is CH or N, n is 0 or 1, R$^1$ is lower alkanyl, lower hydroxy alkyl, phenyl or phenyl loweer alkyl wherein the phenyl groups are unsubstituted or substituted with up to 3 halogen atoms, R$^2$ is aryl, aryloxy, arylthio, aryl lower alkyloxy or aryl lower alkylthio, wherein aryl is phenyl, thienyl or halothienyl, the phenyl group being unsubstituted or substituted with up to 3 halogen atoms and R$^3$ is hydrogen, lower alkynyl, lower alkoxycarbonyl or phenyl, the phenyl group being unsubstituted or substituted with up to 3 substituents, each independently selected from the group consisting of halogen and trifluoromethyl.

3. A composition according to claim 2 in which Q is CH, n is 1, R$^1$ is mono or dihalophenyl, R$^2$ is (mono or dihalophenyl) methoxy and R$^3$ is hydrogen or a pharmaceutically acceptable acid addition salt thereof.

4. A composition according to claim 3 in which the azole compound is 1-{2-(2,4-dichlorophenyl)-2-[2,4- dichlorophenyl)methoxy]ethyl}-1H-imidazale nitrate micronazole nitrate).

5. A composition according to claim 3 in which the azole compound is 1-{2-(2,4-dichlorophenyl)-2-[(4-chlorophenymethoxy]ethyl}-1H-imidazole nitrate (econazole nitrate).

6. A composition according to claim 2 in which Q is CH, n is 0 $R^1$ is mono- or dihalophenyl, $R^2$ and $R^3$ are phenyl.

7. A composition according to claim 6 in which the azole compound is 1{(2-chlorophenyl)diphenyl methyl}-1H-amidazole (clotrimazole).

8. A composition according to claim 1 wherein the azole is a compound of the formula (II)

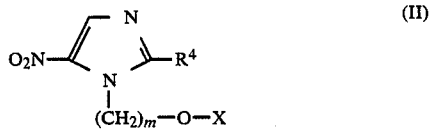

or a pharmaceutically acceptable acid addition salt thereof wherein $R^4$ is hydrogel or lower alkyl, m is 2 to 4 and X is hydrogen or an acyl residue of a monocarboxylic or dicarboxylic aliphotic acid or aromatic acid.

9. A composition according to claim 8 in which the azole compound is 1-(2-hydroxyethyl)-2-methyl-5-nitroimidazole (metronidazole).

10. A composition according to claim 1 in which the mixture contains from 0.1 to 10% by weight of the silver compound and from 0.1 to 10% by weight of the azole compound or pharmaceutically acceptable acid addition salt thereof.

11. A composition according to claim 10 in which the mixture contains from 0.2 to 5% by weight of the silver compound and from 0.2 to 5% by weight of the azole compound or pharmaceutically acceptable acid addition salt thereof.

12. A composition according to claim 11 in which the mixture contains from 0.5 to 3% by weight of the silver compound and from 0.5 to 3% by weight of the azole compound or pharmaceutically acceptable acid addition salt thereof.

13. A composition according to claim 1 in which the silver compound is a silver sulphanamide.

14. A composition according to claim 13 in which the silver compound is silver sulphadiazine.

15. A composition according to claim 1 which is in the form of a hydrophilic ointment.

16. A composition according to claim 1 which is in the form of a hydrophobic ointment.

17. A composition according to claim 1 which is in the form of a tablet.

18. A composition according to claim 1 which is in the form of a pessary.

19. A composition according to claim 1 which is in the form of an aqueous gel.

20. A composition according to claim 1 wherein the weight ratio is 5:1 to 1:5.

21. A composition according to claim 1 wherein the weight ratio is 2:1 to 1:1.

22. A composition according to claim 1 wherein the weight ratio is 1:1.

23. A method of treating burns, ulcers or other skin lesions which comprises applying topically thereto a pharmaceutical composition in topical administration form which comprises a synergistic mixture of an antimicrobial silver compound and an antimicrobial azole compound or a pharmaceutically acceptable acid addition salt thereof in the weight ratio of 10:1 to 1:10 in combination with a topically acceptable carrier therefor.

24. A method according to claim 23 wherein the weight ratio is 5:1 to 1:5.

25. A method according to claim 23 wherein the weight ratio is 2:1 to 1:2.

26. A method according to claim 23 wherein the weight ratio is 1:1.

* * * * *